United States Patent [19]

Ball

[11] Patent Number: 5,057,436
[45] Date of Patent: Oct. 15, 1991

[54] METHOD AND APPARATUS FOR DETECTING TOXIC GASES

[75] Inventor: Dean M. Ball, Gainesville, Ga.

[73] Assignee: AgMaster, Inc., Gainesville, Ga.

[21] Appl. No.: 415,864

[22] Filed: Oct. 2, 1989

[51] Int. Cl.$^5$ .......................................... G01N 30/00
[52] U.S. Cl. .................................... 436/113; 436/151;
   436/147; 422/90; 422/93; 422/98; 422/69;
   422/88; 338/34; 73/31.06
[58] Field of Search ...................... 422/90, 93, 98, 83,
   422/69, 88; 436/113, 151, 147; 338/34; 73/27 R

[56] References Cited

U.S. PATENT DOCUMENTS

| | | | |
|---|---|---|---|
| 2,652,716 | 9/1953 | Blears et al. | 73/27 R |
| 2,984,240 | 5/1961 | Eams | 128/185 |
| 2,993,832 | 7/1961 | Kaitz | 167/53.1 |
| 3,942,479 | 3/1976 | Powers | 119/52 |
| 3,977,836 | 8/1976 | Matsuda et al. | 422/83 |
| 4,107,268 | 8/1978 | O'Neill et al. | |
| 4,305,347 | 12/1981 | Hemenway et al. | 119/15 |
| 4,357,903 | 11/1982 | Moss et al. | 119/15 |
| 4,571,543 | 2/1986 | Raymond et al. | 324/425 |
| 4,574,264 | 3/1986 | Takahashi et al. | 338/34 |
| 4,654,624 | 3/1987 | Hagan et al. | 338/34 |
| 4,670,405 | 6/1987 | Stetter et al. | 436/151 |
| 4,706,493 | 11/1987 | Chang et al. | 73/23 |
| 4,722,905 | 2/1988 | Honeybourne et al. | 436/151 |
| 4,755,473 | 7/1988 | Nishino et al. | 436/133 |

FOREIGN PATENT DOCUMENTS 53-113593 10/1978 Japan .................................... 422/83

Primary Examiner—David L. Lacey
Assistant Examiner—Abanti B. Singla
Attorney, Agent, or Firm—Kennedy & Kennedy

[57] ABSTRACT

Apparatus for detecting the level of ammonia in air comprises a conduit through which air is flowed as an airstream past two ammonia sensors that straddle an ammonia absorber. The apparatus also comprises a signal processing circuit for comparing signals generated by the two ammonia sensors with the difference representing the level of ammonia present in the air.

3 Claims, 1 Drawing Sheet

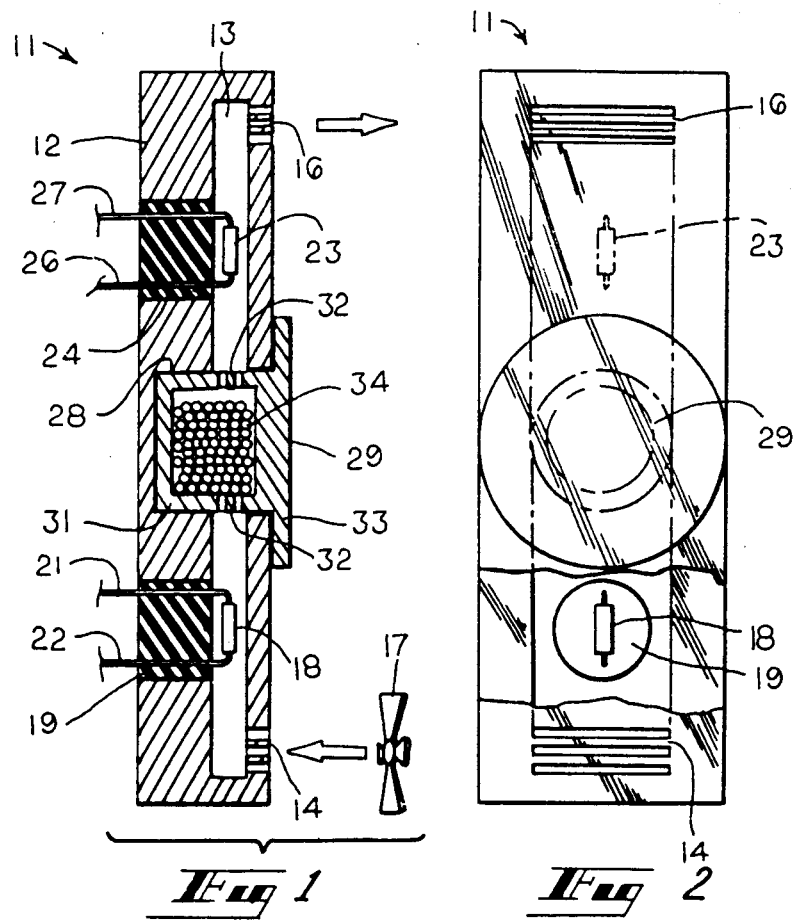
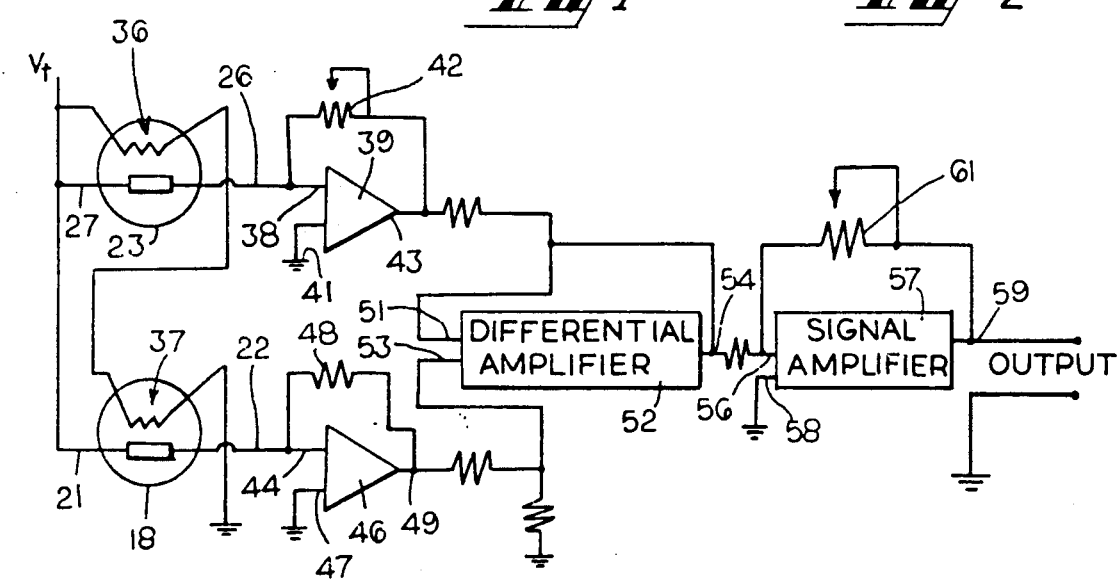

METHOD AND APPARATUS FOR DETECTING TOXIC GASES

TECHNICAL FIELD

This invention relates to the detection of air pollutants, and particularly to methods and apparatuses for detecting the presence of toxic gases, particularly ammonia, in air.

BACKGROUND OF THE INVENTION

Contamination of the air by toxic gases, especially ammonia gas, is a common problem in both agricultural and industrial environments. For example, personnel engaged in the production of blueprints from drawings are exposed to heavy concentrations of ammonia, as generally are those persons engaged in the production or manufacture of fertilizers.

In those situations where animals or poultry are grown or kept in confined quarters, the anaerobic decomposition of their own fecal matter results in a constant exposure of the poultry to concentrations of ammonia that can seriously impair their health, there being a large catalog of ailments attributable to such concentrations. In a copending U.S. Pat. application, Ser. No. 202,557 of D. Ball, filed June 6, 1988, there is disclosed a method and apparatus for monitoring the air within the confined animal quarters for the presence of ammonia and for effectively neutralizing the ammonia in response to detection of concentrations above a threshold quantitative level. The ammonia is generally neutralized by the introduction of a carboxylic acid such as acetic or formic acid into the air.

In general, there are two principal types of ammonia sensors in use, metal oxide semiconductor (MOS) and electrochemical. The MOS sensor generally consists of a heated cylinder of tin oxide doped with an appropriate doping agent, the electrical resistance of which decreases in the presence of ammonia or other organic combustible gases. Such MOS sensors do not discriminate effectively among the several such gases, and they can be affected by changes in temperature and humidity. On the other hand, such sensors are relatively low cost, virtually indestructible and have extended lifetimes, e.g. five to ten years.

Electrochemical ammonia sensors usually consist of a pair of electrodes, a gas permeable membrane, and an electrolyte that is selectively responsive to ammonia. Such sensors generally are not responsive to other organic gases and are unaffected by temperature and humidity changes. On the other hand, they have lifetimes measured in months instead of years, and are considerably more expensive than MOS sensors.

SUMMARY OF THE INVENTION

The present invention is an apparatus which combines advantages of MOS sensors, i.e., long life and low cost, with advantages of electrochemical sensors, i.e., selectivity toward ammonia and relative insensitivity to changes in humidity and temperature.

In an illustrative embodiment of the invention, a housing has an air passage extending therethrough and an air inlet at one end of the passage and an air outlet at the other end thereof. A first MOS sensor is mounted in the housing and extends into the air passage in the vicinity of the air inlet, and a second MOS sensor is mounted in the housing and extends into the air passage in the vicinity of the air outlet. A vented cartridge containing a granular ammonia absorbent extends across the air passage in the region between the two sensors in a manner such that air flowing in the passage is forced to pass through the ammonia absorbent. Means are provided for creating an air flow from inlet to outlet, such as heating means for creating a convective air flow.

Output signals from the two detectors are compared and a difference signal generated which is indicative of the amount of ammonia in the air. This difference signal may be applied to ammonia control means, such as to the timer of the control circuit shown in the aforementioned D. Ball application Ser. No. 202,557.

The various features of the present invention, and advantages thereof will be apparent from the following detailed description, read in conjunction with the accompanying drawings.

BRIEF DESCRIPTION OF THE DRAWING

FIG. 1 is a side elevation, cross-sectional view of apparatus embodying principles of the invention in a preferred form.

FIG. 2 is a partial cut-away plan view of the apparatus of FIG. 1.

FIG. 3 is a schematic diagram of a signal evaluating circuit for the apparatus of FIGS. 1 and 2.

DETAILED DESCRIPTION

FIGS. 1 and 2 depict detecting apparatus 11 of the present invention, which apparatus comprises an elongated housing 12 of suitable material, such as copper or aluminum, having an air passage 13 therein. Air passage 13 extends between an air inlet 14, at one end of the housing 12, and which may comprise a plurality of elongated slots, as shown, and an air outlet at the other end of the housing, which also may comprise a plurality of elongated slots. Suitable means, symbolically depicted by a fan 17, are provided for creating an air flow through passage 13 from inlet 14 to outlet 16. The means 17 may be a fan or an air pump, or it may be means for heating the housing 12 to create a convective air flow between the inlet and the outlet with the housing oriented uprightly.

A first MOS sensor 18 is mounted to a member 19 of insulating material which in turn is mounted in housing 12 in the vicinity of air inlet 14 so that sensor 18 extends into passage 13. Electrical leads 21 and 22 extend from sensor 18 through member 19 and are connected to suitable signal evaluation circuitry and voltage sources, as will be discussed hereinafter. In like manner, a second MOS sensor 23 is mounted in an insulating member 24 through which leads 26 and 27 extend.

Housing 12 is provided with a bore 28 located approximately midway between sensors 18 and 23 into which an absorber module or cartridge 29 is fitted. Cartridge 29 comprises a hollow absorber containing member 31 having slots 32 in the walls thereof to allow for a continuous flow of air in passage 13, and an integral cap 33. Cartridge or module 29 may be of any suitable material, such as plastic or metal. Member 31 is filled with an absorbent material 34 for removing ammonia from the air flowing in passage 13, which may comprise a non volatile acid, such as phosphoric acid, supported upon a bed of granular, porous material.

In FIG. 3 there is shown a schematic diagram of the sensors 18 and 23 coupled to signal evaluation circuit means for generating an output signal indicative of the amount of ammonia pollutant in the ambient air. A heating circuit for heating sensors 23 and 18 comprises heaters 36 and 37 connected in series between a voltage source Vt and ground for maintaining sensors 23 and 18 at an elevated temperature. The elevated temperature is such that any changes in ambient temperature constitute only very small percentages of the total sensor temperature, and thus the effect on the sensors of such changes is minimal. What little effect there is affects both sensors equally, which, as will be understood from the following description, insures that a balance between the sensors is maintained.

Sensor 23 is connected between voltage source $V_t$ and the negative input terminal 38 of an operational amplifier 39, the positive input terminal 41 of which is connected to ground. Amplifier 39, in this configuration, functions as a current to voltage converter. A calibrating potentiometer 42 is connected between output terminal 43 of amplifier 39 and input terminal 38. In the same manner, the output of sensor 18 is applied to the negative input terminal 44 of operational amplifier 46, the positive input terminal 47 of which is connected to ground. A resistor 48, which may be adjustable, is connected between the output terminal 49 of amplifier 46 and input terminal 44. Amplifier 46 also functions as a current to voltage converter in the same manner as amplifier 39. The output terminal 43 of amplifier 39 is connected to a first input terminal 51 of a differential amplifier 52, and the output terminal 49 is connected to a second input terminal 53. The output terminal 54 of amplifier 52 is connected to an input terminal 56 of a signal amplifier 57, the other input terminal 58 of which is connected to ground. Connected between the output terminal 59 of amplifier 57 and signal input terminal 56 is a gain adjusting potentiometer 61.

The detecting apparatus 11 of FIGS. 1 and 2 and the circuit of FIG. 3 may be constructed as a single unitary structure, although the circuit of FIG. 3 is simply an example of a signal processing circuit for the apparatus 11. It is, of course, possible to use other circuit configurations which respond to the operation and output of the apparatus 11.

OPERATION

Where the apparatus 11 is introduced into an environment where it is desired to monitor the amount of pollution such as ammonia gas in the air, its operation to be described hereinafter will be little effected by temperature and humidity changes, inasmuch as both sensors 18 and 23 will be affected equally. The circuitry of FIG. 3 is preferably calibrated and adjusted to produce zero signal output where non-polluted air is directed through passage 13.

Ambient air is directed into apparatus 11 through input 14, and flows along passage 13 past sensor 18, which, in the presence of a polluting gas, responds to generate an output by virtue of the pollutant induced reduction in its resistance. The air stream then passes through slotted member 31 of cartridge 29, the absorbent material 34 therein acting to remove ammonia from the airstream. The air stream then flows past sensor 23, which, because the ammonia is now largely absent from the flowing air, undergoes a lesser reduction in resistance than does sensor 18, thereby generating a signal that differs from the signal generated by sensor 18. The signals thus generated are compared in the circuit of FIG. 3, and the difference between them, which is a measure of the amount of ammonia gas in the air entering apparatus 11, is amplified and applied to a suitable control system, such as that shown in the aforementioned application Ser. No. 202,557 of Ball, to control as by reducing the level of ammonia in the air.

As pointed out before, MOS sensors react to a number of different gases, such as methane, ethane, propane, carbon monoxide, and other organic gases, as well as to ammonia. Any of these other gases present in the air flowing through apparatus 11 will affect sensors 18 and 23 in the same way and to the same degree but will not be absorbed by the ammonia absorbent material 34. Hence, their presence will not result in an output signal being generated. On the other hand, if the conditions of the environment are such that, in addition to ammonia, one or more of these other pollutants may be present in toxic amounts, the absorbing material 34 can be had to include absorbent material for such other gases as well. In that event control signals are produced which are indicative of the amounts of both gases. As yet another alternative, the absorbent material may be only that which absorbs gases other than ammonia.

From the foregoing it can be appreciated that the present invention retains the desirable features of both MOS and electrochemical sensors, without their disadvantages, in the reliable detection of the amount of ammonia gas in the ambient air. Only one preferred embodiment of the invention has been shown, but it should be understood that numerous modifications, additions, and deletions may occur to workers in the art without departure from the spirit and scope of the invention.

I claim:

1. Apparatus for determining the level of ammonia in ambient air comprising
    a member having an air passage extending therethrough having an inlet and an outlet,
    first and second detecting means responsive to the presence of ammonia in the air for generating electric signals indicative of the amount of ammonia detected in the air, said first and second detecting means being spaced apart along said air passage with said first detecting means located adjacent said air passage inlet and said second detecting means located adjacent said air passage outlet,
    absorbing means for absorbing at least a portion of ammonia in the air located in said air passage between said first and second detecting means, said absorbing means comprises a non-volatile acid that reacts with ammonia,
    means for creating a continuous flow of air through said air passage over said non-volatile acid and said first and second detecting means, and
    means for evaluating any differences in the electric signals from said first and second detecting means and for producing an output signal indicative of the presence of ammonia.

2. The apparatus of claim 1 wherein each of said detector means comprises a metal oxide semiconductor.

3. The apparatus of claim 1 wherein said air flow creating means comprises means for heating each of said detector means.

* * * * *